United States Patent
Stolen et al.

(10) Patent No.: US 9,744,348 B2
(45) Date of Patent: Aug. 29, 2017

(54) IMPLANTABLE LEADS WITH TOPOGRAPHIC FEATURES FOR CELLULAR MODULATION AND RELATED METHODS

(75) Inventors: Craig M. Stolen, New Brighton, MN (US); Mark J. Schwartz, White Bear Lake, MN (US); John D. Foley, Lino Lakes, MN (US); Lili Liu, Maple Grove, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 1694 days.

(21) Appl. No.: 11/842,565

(22) Filed: Aug. 21, 2007

(65) Prior Publication Data
US 2009/0054960 A1    Feb. 26, 2009

(51) Int. Cl.
*A61N 1/00*     (2006.01)
*A61N 1/05*     (2006.01)
*A61B 18/14*    (2006.01)
*A61B 18/00*    (2006.01)

(52) U.S. Cl.
CPC .......... *A61N 1/056* (2013.01); *A61B 18/1492* (2013.01); *A61B 2018/00125* (2013.01); *A61N 1/0565* (2013.01); *A61N 2001/0578* (2013.01)

(58) Field of Classification Search
CPC   A61B 2018/00059; A61B 2018/00065; A61B 2018/00107; A61B 2018/00125
USPC ................ 607/116–117, 126; 600/373–382; 604/175
See application file for complete search history.

(56) References Cited

U.S. PATENT DOCUMENTS

| | | | |
|---|---|---|---|
| 4,101,984 A | 7/1978 | MacGregor | |
| 5,318,572 A | 6/1994 | Helland et al. | |
| 5,520,664 A * | 5/1996 | Bricault et al. | 604/265 |
| 5,964,794 A | 10/1999 | Bolz et al. | |
| 5,984,896 A * | 11/1999 | Boyd | 604/175 |
| 6,078,840 A * | 6/2000 | Stokes | 607/127 |
| 6,304,786 B1 * | 10/2001 | Heil et al. | 607/126 |

(Continued)

OTHER PUBLICATIONS

Deligianni, Despina D. et al., Effect of surface roughness of hydroxyapatite on human bone marrow cell adhesion, proliferation, differentiation and detachment strength, Nov. 1, 1999, Biomaterials 22 (2001) 87-96.*

(Continued)

*Primary Examiner* — Eric D. Bertram
*Assistant Examiner* — Elizabeth K So
(74) *Attorney, Agent, or Firm* — Faegre Baker Daniel LLP

(57) ABSTRACT

Embodiments of the invention are related to leads with topographic surface features and related methods, amongst other things. In an embodiment, the invention includes an implantable lead including a lead body having a proximal end and a distal end, the lead body including an outer layer defining a lumen, the lead body further including a first electrical conductor disposed within the lumen of the outer layer. The implantable lead can further include a first electrode coupled to the lead body, the electrode in electrical communication with the first electrical conductor. The implantable lead can also include a cellular modulation segment on the external surface of the lead body, the cellular modulation segment comprising topographic surface features configured to modulate cellular responses. Other embodiments are also included herein.

11 Claims, 13 Drawing Sheets

(56) References Cited

U.S. PATENT DOCUMENTS

| | | | |
|---|---|---|---|
| 6,792,318 B2* | 9/2004 | Chitre et al. | 607/126 |
| 7,463,933 B2* | 12/2008 | Wahlstrom et al. | 607/126 |
| 2003/0233139 A1 | 12/2003 | Chitre et al. | |
| 2004/0215306 A1 | 10/2004 | Heil, Jr. et al. | |
| 2005/0038498 A1 | 2/2005 | Dubrow et al. | |
| 2005/0084672 A1 | 4/2005 | O'Brian | |
| 2005/0112349 A1 | 5/2005 | Laurencin et al. | |
| 2005/0119718 A1 | 6/2005 | Coe et al. | |
| 2005/0221271 A1 | 10/2005 | Murphy et al. | |
| 2005/0287186 A1 | 12/2005 | Ellis-Behnke et al. | |
| 2006/0068090 A1 | 3/2006 | Monbouquette et al. | |
| 2006/0085063 A1 | 4/2006 | Shastri et al. | |
| 2006/0121080 A1 | 6/2006 | Lye et al. | |

OTHER PUBLICATIONS

Abrams, G. A. et al., "Electron Microscopy of the Canine Corneal Basement Membranes", *Cells Tissues Organs* 2002 , 170: 251-257.
Abrams, et al., "Nanoscale Topography of the Basement Membrane Underlying the Corneal Epithelium or the Rhesus Macaque", *Cell Tissue Res* 2000 , 299: 39-46.
Abrams, G. A. et al., "Nanoscale Topography of the Corneal Epithelial Basement Membrane and Descemet's Membrane of the Human", *Cornea* 2000 , 19: 57-64.
Abrams, G. A. et al., "The Effects of Substratum Topography on Cell Behavior", *Biomimetic Materials and Design* Marcel Dekker, Inc.: New York, NY 2002 , 91-138.
Brody, Sarah et al., "Characterizing Nanoscale Topography of the Aortic Heart Valve Basement Membrane for Tissue Engineering Heart Valve Scaffold Design", *Tissue Engineering* 2006 , vol. 12, No. 2: 413-421.
Charest, Joseph L. et al., "Myoblast Alignment and Differentiation on Cell Culture Substrates With Microscale Topography and Model Chemistries", *Biomaterials* 2007 , 28: 2202-2210.
Chung, T. W. et al., "Enhancement of the Growth of Human Endothelial Cells by Surface Roughness at Nanometer Scale", *Biomaterials* 2003 , 24(25): 4655-4661.
Clark, P. et al., "Cell Guidance by Ultrafine Topography In Vitro", *J. Cell Sci.* 1991 , 99: 73-77.
Curtis, A. et al., "Topographical Control of Cells", *Biomaterials* 1997 , 18: 1573-1583.
Dalby, M. J. et al., "Polymer-Demixed Nanotopography: Control of Fibroblast Spreading and Proliferation", *Tissue Eng* 2002 , 8(6): 1099-1108.
Diehl, K. A. et al., "Nanoscale Topography Modulates Corneal Epithelial Cell Migration", *J. Biomed Mater Res A* 2005 , 75(3): 603-611.
Fan, Y. W. et al., "Culture of Neural Cells on Silicon Wafers with Nano-Scale Surface Topograph", *J. Neurosci Methods* 2002 , 120(1): 17-23.
Foley, J. D. et al., "Cooperative Modulation of Neuritogenesis by PC12 Cells by Topography and Nerve Growth Factor", *Biomaterials* 2005 , 26(17): 3639-3644.
Kane, Ravi S. et al., "Patterning Proteins and Cells Using Soft Lithography", *Biomaterials* 1999 , 20: 2363-2376.
Karuri, N. W. et al., "Biological Length Scale Topography Enhances Cell-Substratum Adhesion of Human corneal Epithelial Cells", *Journal of Cell Science* 2004 , 117(15): 3153-3164.
Liliensiek, S. J. et al., "The Scale of Substratum Topographic Features Modulates Proliferation of Corneal Epithelial Cells and Corneal Fibroblasts", *Journal of Biomedical Materials Research Part A* www.interscience.wiley.com 2006 , 185-192.
Sack, S. et al., "Stimulation of the Left Ventricle Through the Coronary Sinus with a Newly Developed 'Over the Wire' Lead System—Early Experiences with Lead Handling and Positioning", *Europace* 2001 , 3: 317-323.
Teixeira, A. I. et al., "Epithelial Contact Guidance on Well-Defined Micro- and Nanostructured Substrates", *J. Cell Sci.* 2003 , 116(Pt 10): 1881-1892.
Teixeira, A. I. et al., "The Effect of Environmental Factors on the Response of Human Corneal Epithelial Cells to Nanoscale Substrate Topography", *Biomaterials* 2006 , 27: 3945-3954.
Washburn, N. R. et al., "High-Throughput Investigation of Osteoblast Response to Polymer Crystallinity: Influence of Nanometer-Scale roughness on Proliferation", *Biomaterials* 2004 , 25(7-8): 1215-1224.
"International Search Report from International application No. PCT/US2008/073160".
Final Office Action mailed Jan. 31, 2011 in co-pending U.S. Appl. No. 11/769,402, "Measurement of Cardiac Performance with Movement Sensors and Related Methods," (12 pages).
"Japanese Office Action", from JP Application No. 2010-521937, corresponding to U.S. Patent, mailed Mar. 29, 2012, (pp. 1-12) Including English translation.
"Japanese Office Action", from JP Application No. 2010-521937, corresponding to U.S. Patent, mailed Mar. 19, 2013, (pp. 1-5) Including English translation.

* cited by examiner

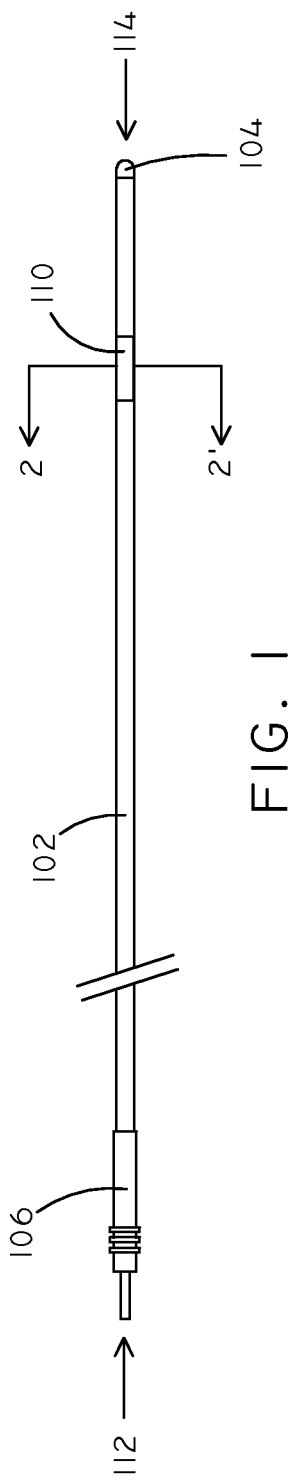
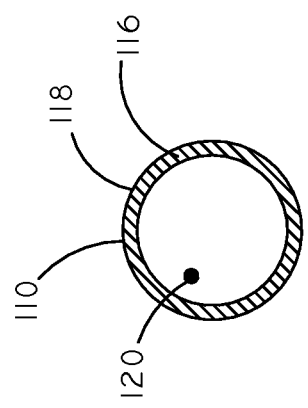

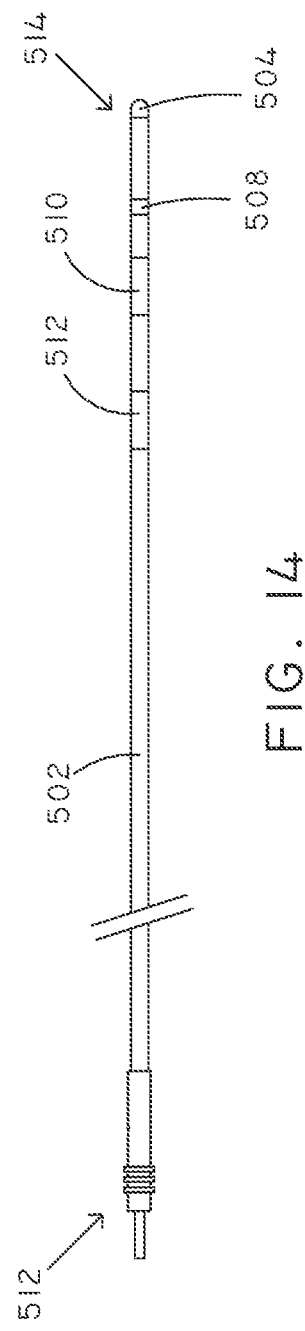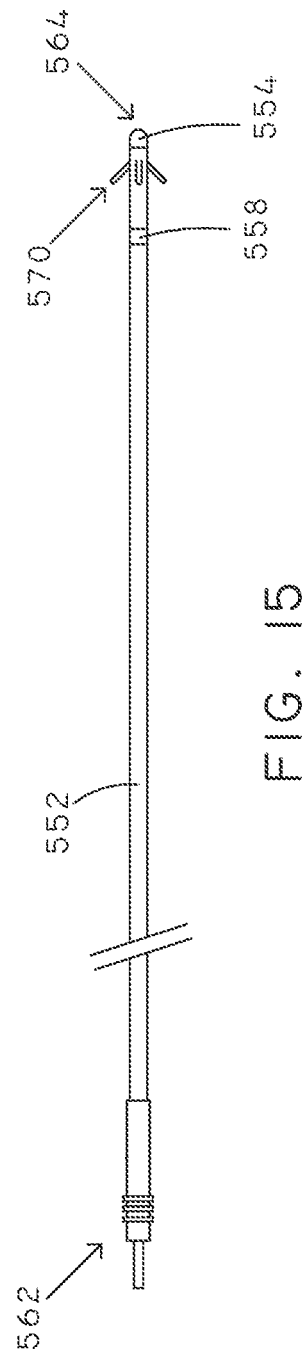

IMPLANTABLE LEADS WITH TOPOGRAPHIC FEATURES FOR CELLULAR MODULATION AND RELATED METHODS

TECHNICAL FIELD

This disclosure relates generally to implantable leads and, more particularly, to implantable leads with topographic surface features, amongst other things.

BACKGROUND OF THE INVENTION

Some types of implantable medical devices are configured to administer electrical stimulation to certain target tissues. As an example, cardiac rhythm management devices can be configured to deliver electrical stimulation pulses to cardiac tissue. As another example, neurological stimulation devices can be configured to deliver electrical stimulation pulses to nervous tissue.

In many cases, the implantable electrical stimulation systems include what is commonly referred to as a pulse generator and leads. The pulse generator is usually a sealed case containing circuitry configured to generate electrical stimulation pulses. These pulses then pass through one or more conductors in the leads before being delivered to a specific target tissue through electrodes that interface with the target tissue.

Frequently, fixation elements are used in conjunction with leads. Fixation elements can aid in keeping an electrode properly engaged with a target tissue for delivery of electrical stimulation. Existing fixation systems can include both active and passive fixation elements. Active fixation elements usually have a component, such as a screw or hook, which is inserted into the target tissue, such as into the myocardium. However, insertion of an active fixation element can sometimes result in undesirable trauma to the target tissue. Passive fixation elements usually include appendages, such as tines, that are designed to lodge in tissue, such as in the trabeculae of the atrium or ventricle. The appendages, in conjunction with tissue that grows around the appendages, function to anchor the electrode in place. However, passive fixation elements are not always effective to secure a lead in place, because of lack of suitable trabeculae in a desired target area and vigorous cardiac wall movement.

In some cases, leads must be removed (explanted) after a period of time in the body of a patient. Reasons for explant procedures can include infection, lead malfunction, lead dislodgement, and the like. However, fibrous tissue sometimes grows around the lead after a period of time due to the human body's immunological response to a foreign body. This fibrous tissue can make it very difficult to remove the old leads, increasing the risks of complications during the explant procedure.

For at least these reasons, a need remains for implantable leads that can be fixed in place. A need also exists for implantable leads that can be explanted while reducing risks of complications.

SUMMARY OF THE INVENTION

Embodiments of the invention are related to leads, such as electrical stimulation leads and sensor leads, with topographic surface features and related methods, amongst other things. In an embodiment, the invention includes an implantable lead including a lead body having a proximal end and a distal end, the lead body including an outer layer defining a lumen, the lead body further including a first electrical conductor disposed within the lumen of the outer layer. The implantable lead can further include a first electrode coupled to the lead body, the electrode in electrical communication with the first electrical conductor. The implantable lead can also include a cellular modulation segment on the external surface of the lead body, the cellular modulation segment comprising topographic surface features configured to modulate cellular responses.

In an embodiment, the invention includes an implantable lead including a lead body having a proximal end and a distal end, the lead body including an outer layer defining a lumen and a first electrical conductor disposed within the lumen of the outer layer. The implantable lead can further include a first electrode positioned at the distal end of the lead body, the electrode in electrical communication with the first electrical conductor. The implantable lead can further include a fixation element coupled to the lead body and a cellular modulation segment disposed on the surface of the fixation element, the cellular modulation segment including topographic surface features configured to modulate cellular responses.

In an embodiment, the invention includes an implantable lead including a lead body having a proximal end and a distal end, the lead body comprising an outer layer defining a lumen, the lead body further including a conductor disposed within the lumen of the outer layer and a cellular modulation segment on the external surface of the lead body, the cellular modulation segment including topographic surface features configured to modulate cellular responses.

In an embodiment, the invention includes a method for making an implantable lead including welding an electrode to a conductor, disposing an outer layer over the conductor, and disposing a cellular modulation segment on the outer layer, the cellular modulation segment comprising topographic surface features configured to modulate cellular responses.

In an embodiment, the invention includes an implantable lead including a lead body having a transmission segment and a distal segment, the distal segment about 10 centimeters to 15 centimeters in length, the transmission segment having a length equal to the remainder of the lead body length. The lead body can also include an outer layer defining a lumen and a first electrical conductor disposed within the lumen of the outer layer. The lead body can also include a first electrode positioned on the distal segment of the lead body, the electrode in electrical communication with the first electrical conductor. The implantable lead can also include a first cellular modulation segment positioned on the distal segment of the lead body, the first cellular modulation segment comprising topographic surface features configured to promote cellular adherence. The implantable lead can also include a second cellular modulation segment positioned on the transmission segment of the lead body, the second cellular modulation segment comprising topographic surface features configured to reduce cellular adherence.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which:

FIG. 1 is a schematic view of a lead in accordance with an embodiment of the invention.

FIG. 2 is a schematic cross-sectional view of a lead as taken along line 2-2' of FIG. 1.

FIG. 14 is a schematic view of a lead in accordance with an embodiment of the invention.

FIG. 15 is a schematic view of a lead in accordance with an embodiment of the invention.

Figure 3:
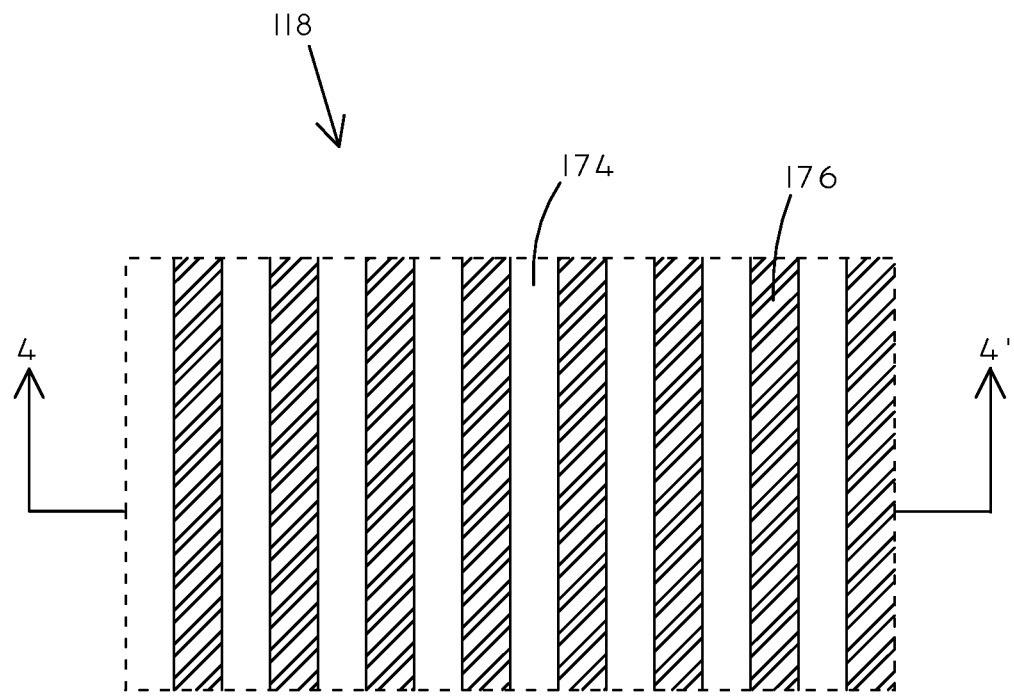
FIG. 3 is a schematic top view of topographic surface features in accordance with an embodiment of the invention.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

Recently it has been demonstrated that topographic surface features can be used in order to modulate the behavior of host tissue cells. By way of example, topographic surface features can be configured to increase or decrease the growth of host tissue cells. As another example, topographic surface features can also be configured to increase or decrease the migration rate of host tissue cells over the surface features. While the mechanisms for these effects are not fully understood, it is believed that these effects are at least partially a result of mimicking topographic features found naturally in the extracellular matrix of host tissues.

Because topographic surface features can be used to modulate the behavior of host tissue cells, such surface features can be disposed on leads, such as electrical stimulation leads and sensor leads, in order to enhance the functionality of leads in various ways. For example, in some embodiments, topographic surface features configured to enhance tissue growth, differentiation, and/or adherence can be used on some parts of a lead in order to aid in anchoring the lead in a desired position within the vasculature of a patient. Conversely, in some embodiments, topographic surface features configured to slow tissue growth and reduce tissue adherence can be used on some parts of a lead in order to aid in making the lead more easily explanted. As such, embodiments of the invention can include leads with topographic surface features, various aspects of which will now be described in greater detail.

Referring now to FIG. 1, a schematic view of a lead is shown in accordance with an embodiment of the invention. The lead includes a lead body 102 with a proximal end 112 and a distal end 114. The lead includes an electrode 104 positioned near the distal end 114. The electrode 104 can include various conductive materials such as platinum, silver, gold, iridium, titanium, and various alloys.

In some embodiments, the lead includes a first electrode, referred to as a tip electrode or distal electrode, and a second electrode, referred to as a ring electrode or proximal electrode, disposed a short distance away. In some embodiments, the lead includes more than two electrodes. It will be appreciated that the lead can be a pacing/sensing lead, defibrillating lead, a sensor lead, or the like. In some embodiments, such as where the lead is to be used for defibrillation in addition to pacing, the lead can also include a coil electrode, referred to as a shocking coil, near the distal end 114 of the lead.

The lead further includes a terminal pin 106 for connecting the lead to an implantable device, such as a cardiac rhythm management (CRM) device. The terminal pin 106 can be compatible with various standards for lead-header interface design including the DF-1, VS-1, IS-1, LV-1 and IS-4 standards.

A cellular modulation segment 110 can be disposed on the lead body 102. The cellular modulation segment 110 can be configured to modulate the behavior of host tissue cells, such as endothelial cells, fibroblasts, myocytes, immune system cells, and the like. By way of example, cellular behavior that can be modulated with topographical features of a cellular modulation segment can include cell shape, cell adherence, cell alignment, cell migration, cell differentiation, cell proliferation, inflammation, and the like. The cellular modulation segment 110 can be configured to modulate (such as increase or decrease) any of these cell behaviors. In some embodiments, the cellular modulation segment surrounds a lead. In some embodiments, the cellular modulation segment covers just one portion or side of a lead. In some embodiments, the cellular modulation segment includes regions of different patterning.

FIG. 2 is a cross-sectional schematic view of a lead as taken along line 2-2' of FIG. 1. The lead includes an outer layer 116 with an outer surface 18. The outer layer 116 can be flexible and can be configured to protect other components disposed within the lumen of the outer layer 116. In some embodiments, the outer layer 116 can be circular in cross-section. In some embodiments, the outer layer 116 includes a dielectric material. In some embodiments, the outer layer 116 can include various biocompatible materials such as polysiloxanes, polyethylenes, polyamides, polyurethane and the like.

A conductor 120 can be disposed within the lumen of the outer layer 116. The conductor 120 can include various materials including copper, aluminum, silver, gold, and various alloys such as tantalum/platinum, MP35N and the like. An insulator (not shown) can surround the conductor 120. The insulator can include various materials such as electrically insulating polymers (such as expanded polytetrafluoroethylene (ePTFE)). In some embodiments, the conductor 120 is configured as a coil or a cable. Multiple conductors can be disposed within the lumen of the outer layer 116. For example, a separate conductor can be in communication with each electrode disposed on the lead. In this embodiment, the outside surface 118 of the outer layer 116 contains the cellular modulation segment 110. In other words, the cellular modulation segment is part of the outer layer itself. As such, the outside surface 118 of outer layer 116 can include topographic surface features. In other embodiments, the segment can be separate from the outer layer, such as existing as a separate layer of material over the outer layer.

It is believed that the scale of topographic features is important to the behavior elicited from host cells. If the scale of topographic features is too large in some dimensions, then the topographic surface features may not have a desired modulating effect on the host cells. Similarly, if the scale of topographic features is too small in some dimensions, then again, the topographic surface features may not have a desired modulating effect on the host cells. In general, the scale of useful topographical features for purposes of cell behavior modulation can be referred to as nanoscale. By way of example, topographical features in some embodiments herein can include features with dimensions of about 10 nm (nanometers) to about 1000 nm. In some embodiments, the topographic features can include dimensions of about 100 nm to about 400 nm.

Referring now to FIG. 3, a top schematic view is shown of topographic surface features 118 in accordance with an embodiment of the invention. The topographic surface features 118 include a plurality of peaks 176 and valleys 174. In this embodiment, the peaks 176 can take on the form of a plurality of ridges, while the valleys 174 can take on the form of a plurality of grooves.

Figure 4:
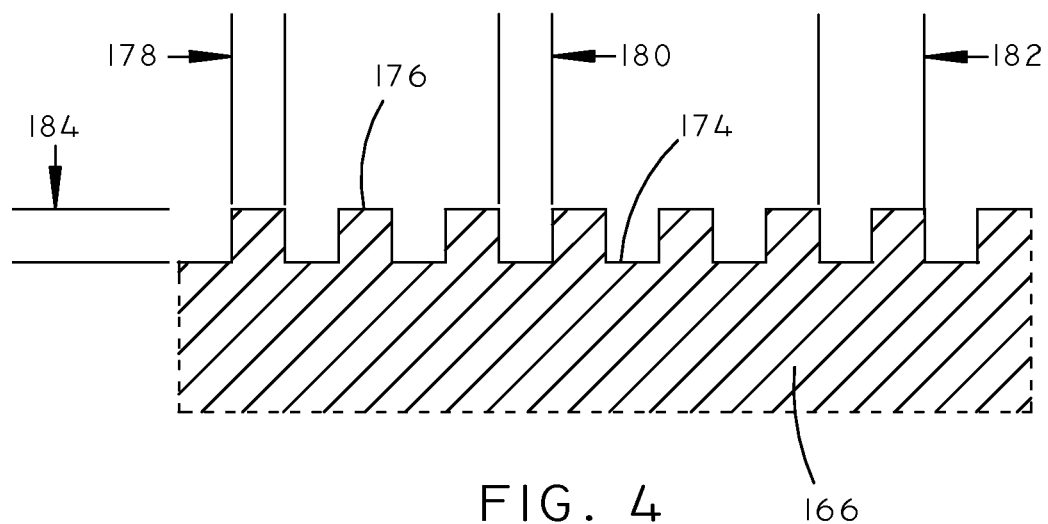
FIG. 4 is a schematic cross-sectional view of topographic surface features as taken along line 4-4' of FIG. 3.

Referring now to FIG. 4, a cross-sectional schematic view is shown of topographic surface features 118 as taken along line 4-4' of FIG. 3. The peaks and valleys are defined by a substrate 166. As can be seen, each of the peaks 176 has a width 178. The width of the peaks 176 can be between about 10 nm and about 1000 nm. Similarly, each of the valleys 174 has a width 180. The width of the valleys 180 can be between about 10 nm and about 1000 nm. The combined width of a peak 176 and a valley 174 can be referred to as the pitch 182. In embodiments herein, the pitch can be between about 20 nm and about 2000 nm.

The vertical distance 184 between the peaks 176 and the valleys 174 can be referred to as the depth of the topographic surface features. In embodiments herein, the depth of the topographic features can be between about 10 nm and about 1000 nm. In some embodiments, the depth of the topographic features is greater than about 300 nm.

In some embodiments, the lead can also include an active agent in order to further modulate cellular behavior. By way of example, an active agent can be included in an active agent elution coating disposed over the topographic surfaces features. The active agent elution coating can be configured to release the active agent over time after the lead is implanted within a patient. Many different examples of active agent elution coatings are well known in the art. The active agent can include matrix proteins, steroids, growth factors, antibiotics, and the like.

Figure 5:
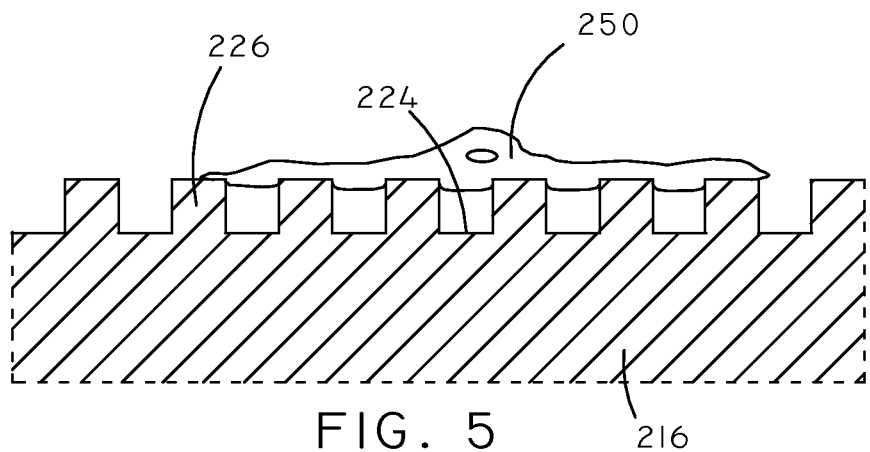
FIG. 5 is a schematic view of a cell disposed over topographic surface features in accordance with an embodiment of the invention.

Referring now to FIG. 5, a cell 250 is shown disposed over peaks 226 and valleys 224 defined by a substrate 216. The behavior of the cell 250 can be modulated by topographic surface features of embodiments of the invention. By way of example, cellular behavior that can be modulated can include cell shape, cell adherence, cell alignment, cell migration, cell differentiation, cell proliferation, and the like. As a specific example, cell adhesion can be enhanced with topographical features such as a plurality of ridges with a pitch of about 250 nm or less. As another example, cell migration can be enhanced with topographical features such as a plurality of ridges with a pitch of between about 750 nm and 850 nm. In some embodiments, topographic surface features can include a multitude of feature sizes that are distributed in a pattern similar to that found in an extracellular matrix.

Figure 6:
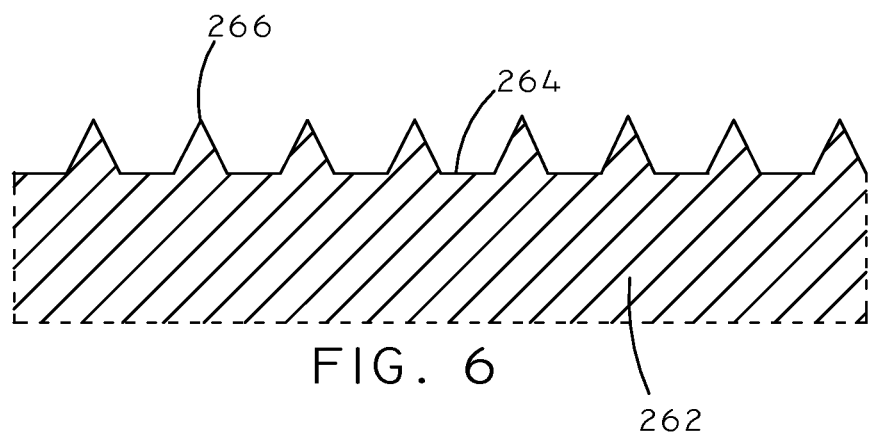
FIG. 6 is a schematic cross-sectional view of topographic features in accordance with an embodiment of the invention.
Figure 7:
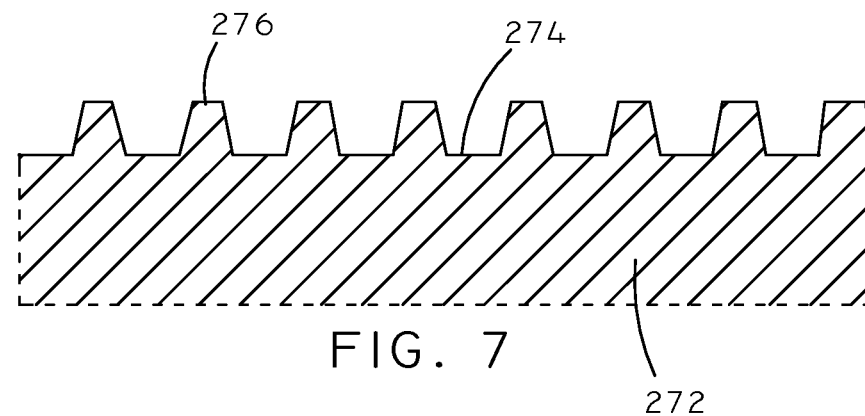
FIG. 7 is a schematic cross-sectional view of topographic features in accordance with an embodiment of the invention.

In addition to the scale of topographical features being relevant to the specific cellular behavior elicited, it is also believed that the morphology of the topographic features can be relevant as well. In this regard, it will be appreciated that topographic features used with embodiments herein can take on many different morphologies in cross-section. By way of example, in FIGS. 3-5, the topographic features are shown with peaks having a square or rectangular profile in cross-section. However, topographical features of the invention can include many other cross-sectional shapes including rounded profiles, polygonal shapes, and irregular shapes. By way of example, referring now to FIG. 6, topographic features with a triangular or saw tooth profile are shown. In FIG. 6, a substrate 262 defines peaks 266 that are triangular in shape and valleys 264 that are flat at the bottom. As another example, referring now to FIG. 7, a substrate 272 defines peaks 276 that are trapezoidal in cross-section and valleys 274 that are flat at the bottom. Many other shapes are contemplated herein.

Figure 8:
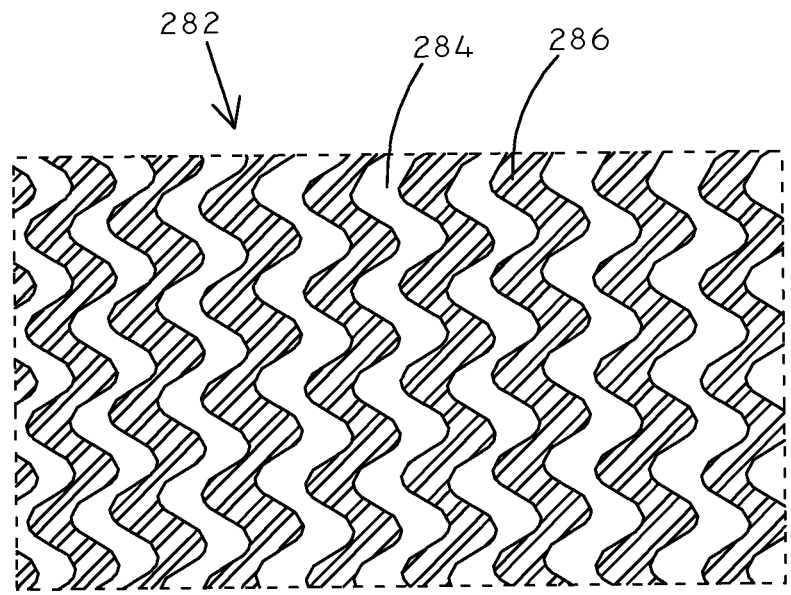
FIG. 8 is a schematic top view of topographic features in accordance with an embodiment of the invention.

Patterns formed by topographical surfaces features of embodiments herein can include uniform and complex patterns in two and/or three dimensions. In some embodiments, the topographic features include ridges that are relatively straight and parallel to one another. Such ridges can be arranged so that they are parallel to the lengthwise axis of the lead, perpendicular to the lengthwise axis of the lead, or some orientation in between. In other embodiments, the topographic features can include ridges that are randomly oriented. In still other embodiments, the topographic surfaces can include ridges that are curvilinear. Referring now to FIG. 8, a top view is shown of topographic surface features 282 in accordance with another embodiment of the invention. The topographic surface features 282 include a plurality of peaks 286 and valleys 284. In this embodiment, both the peaks and valleys are curvilinear. Many other arrangements of peaks and valleys are also contemplated herein.

Figure 9:
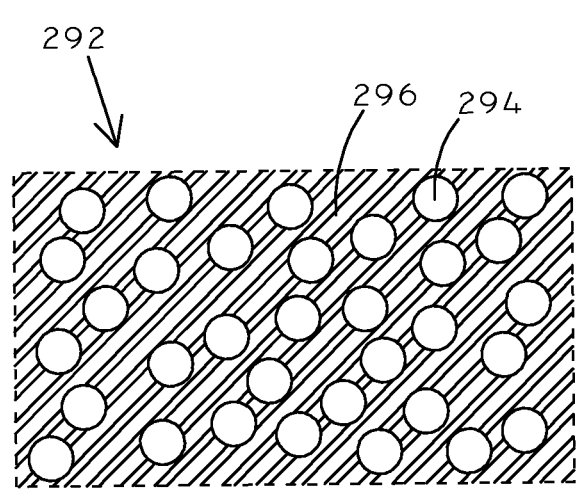
FIG. 9 is a schematic top view of topographic features in accordance with an embodiment of the invention.

In some embodiments, topographic surface features in accordance with embodiments of the invention can take on configurations other than ridges. For example, in some embodiments, topographic surface features can be characterized by a plurality of pits or pores. Referring now to FIG. 9, a top view is shown of topographic surface features 292 in accordance with another embodiment of the invention. The surface features 292 include a plurality of pores 294 disposed on a surface 296. The pores can be of various diameters in order to mimic features of the extracellular matrix of host tissue. In some embodiments, the diameter of the pores 294 can be from about 20 nm to about 120 nm.

Figure 10:
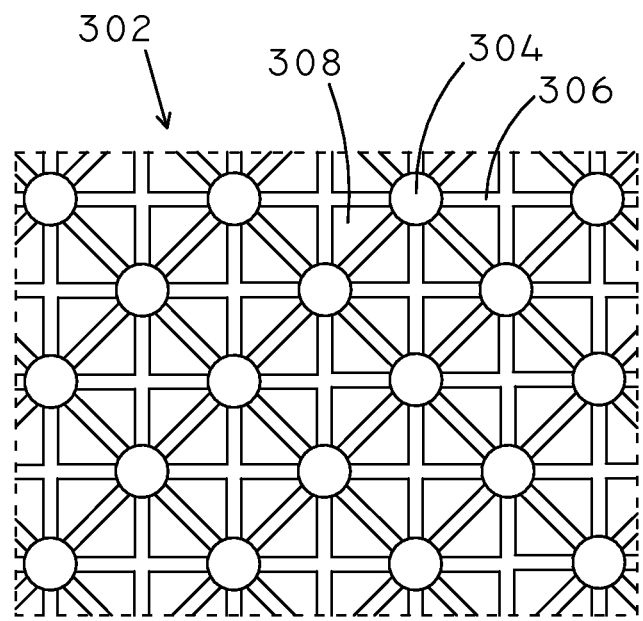
FIG. 10 is a schematic top view of topographic features in accordance with an embodiment of the invention.

Referring now to FIG. 10, a schematic top view is shown of topographic surface features 302 in accordance with another embodiment of the invention. The topographic surface features 302 include a lattice-type structure with a plurality of nodes 304 and interconnecting ridges 306. The nodes 304 and interconnecting ridges 306 are raised above an underlying basement layer 308. It will be appreciated that many other configurations of topographic features are also included herein.

Figure 11:
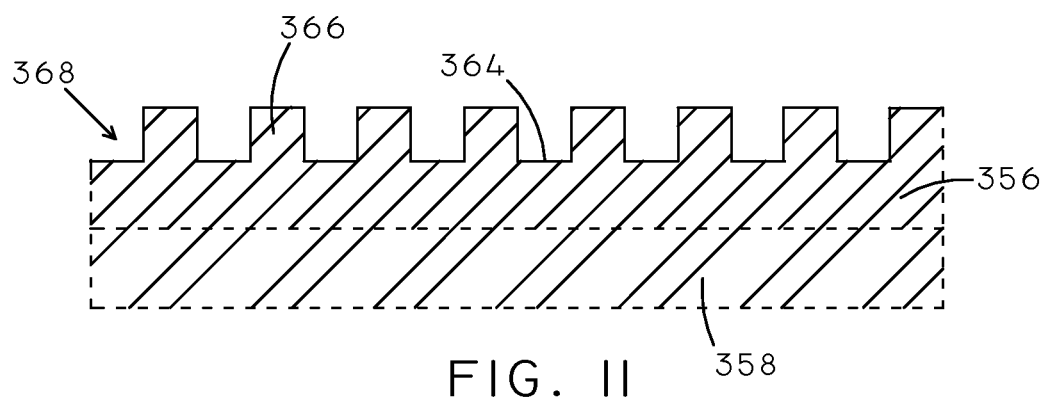
FIG. 11 is a schematic cross-sectional view of a cellular modulation segment disposed over an outer layer in accordance with an embodiment of the invention.
Figure 12:
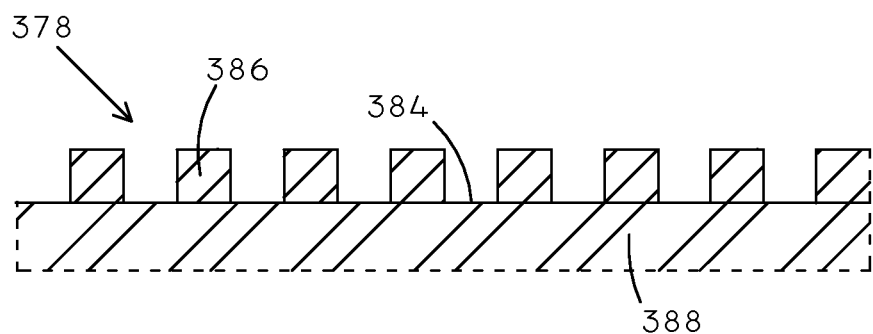
FIG. 12 is a schematic cross-sectional view of a cellular modulation segment disposed over an outer layer in accordance with an embodiment of the invention.

In some embodiments, the topographic surface features can be part of the outer layer itself. In other embodiments, the topographic surface features can be part of a separate element overlying the outer layer. For example, referring now to FIG. 11, a cross-sectional view is shown of a cellular modulation segment 368 disposed over an outer layer 358. The cellular modulation segment 368 can include a substrate 356 that defines a plurality of peaks 366 and valleys 364. The substrate 356 can be a material such as a polymer, a metal, a ceramic, and the like. The substrate 356 can be mechanically affixed to the outer layer 358 of a lead. In some embodiments, the substrate 356 can be adhered to the outer layer 358 with an adhesive. In some embodiments, the substrate 356 can be welded to the outer layer 358. Referring now to FIG. 12, another embodiment of a cellular modulation segment 378 overlying an outer layer 388 is shown. The cellular modulation segment 378 can include a plurality of peaks 386 or bumps. The peaks 386 are separate from one another in cross-section and the outer layer 388 itself forms valleys 384.

Figure 13:
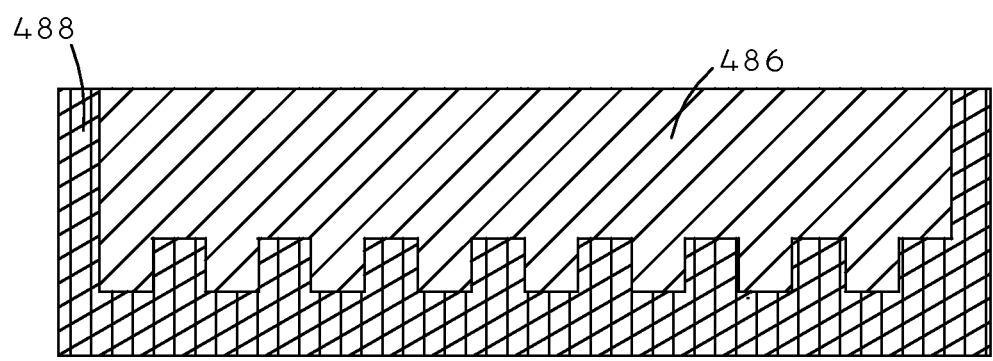
FIG. 13 is a schematic cross-sectional view of a substrate with topographic features disposed within a component of a molding apparatus.

Topographic surfaces features of embodiments of the invention can be formed in many different ways. By way of example, in some embodiments, topographic features can be formed using techniques such as molding, etching, lithographic etching, spray coating, micro-contact printing, nano-blasting or the like. Referring now to FIG. 13, a cross-sectional view is shown of a substrate with topographic features in conjunction with a mold. The mold 488 has features that are the opposite in shape of what is desired for the topographic features. The mold 488 can include a material that can retain structural integrity under conditions sufficient to mold the substrate 486. The substrate material 486 can be poured into the cavity of the mold 488 as a molten material (such as in the case of a metal or a thermoplastic polymer) or an uncured composition (such as in the case of a polymer) and then hardened and/or solidified while in the mold 488. In some embodiments, the substrate material 486 can be pressed into the mold 488 and assume the reciprocal form as the mold 488. It will be appreciated that many other techniques can also be used to form topographic surface features in accord with embodiments of the invention.

It will be appreciated that leads with topographic surface features as described herein can include one or more cellular modulation segments. Referring now to FIG. 14, a schematic view is shown of a lead in accordance with another embodiment of the invention. The lead includes a lead body 502 with a proximal end 512 and a distal end 514. The lead includes a first electrode 504, or tip electrode, positioned near the distal end 514. The lead also includes a second electrode 508, or ring electrode, positioned a short distance away from the first electrode 504.

The lead includes a first cellular modulation segment 510 and a second cellular modulation segment 512. The first and second cellular modulation segments 510, 512 can include topographical surface features configured to modify the behavior of host cells. The topographical surface features of the first cellular modulation segment 510 can be either the same or different than the topographical surface features of the second cellular modulation path 512. For example, in some embodiments, the first cellular modulation segment 510 can be designed to be disposed in an area of vasculature where increased cellular adherence is desirable and therefore the first cellular modulation segment 510 can include a surface topology configured to enhance cellular adherence. In contrast, the second cellular modulation segment 512 can be designed to be disposed in an area of the vasculature where cellular adherence is not desirable and therefore the second cellular modulation segment 512 can include a surface topology configured to reduce cellular adherence.

The interface of electrodes with target tissues can be enhanced in some cases by modulating cellular responses of the target tissue. As such, in some embodiments, surfaces of the first electrode 504 and/or the second electrode 508 can include a surface topology configured to modulate cellular responses. By way of example, a cellular modulation segment can be disposed on an electrode. In some embodiments a cellular modulation segment with topographic surface features configured to prevent the formation of fibrotic tissue surrounding the electrode can be disposed on an electrode. In some embodiments, the cellular modulation segment can be part of the electrode itself and can include an electrically conductive material.

In some embodiments, at least about 10% of the surface area of the lead body of a lead can be covered with topographic surface features, such as those described herein. In some embodiments, at least about 25% of the surface area of the lead body of a lead can be covered with topographic surface features, such as those described herein. In some embodiments, at least about 50% of the surface area of the lead body of a lead can be covered with topographic surface features, such as those described herein.

Figure 16:
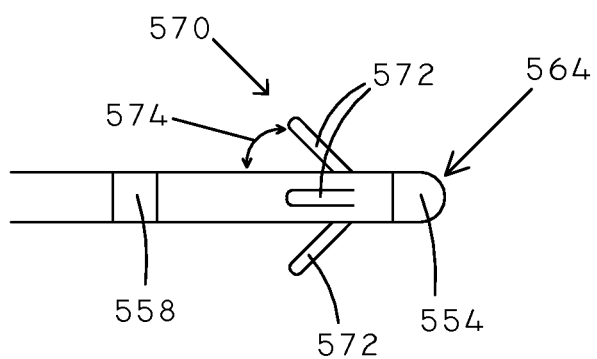
FIG. 16 is an enlarged view of a portion of the lead of FIG. 15.

Some embodiments of the invention can include leads with topographical features located on fixation elements. Referring now to FIG. 15, an embodiment of a lead is shown in accordance with another embodiment of the invention. The lead includes a lead body 552 with a proximal end 562 and a distal end 564. The lead includes a first electrode 554, or tip electrode, positioned near the distal end 564. The lead also includes a second electrode 558, or ring electrode, positioned a short distance away from the first electrode 554. The lead also includes a fixation element 570. Referring now to FIG. 16, an enlarged portion of the lead of FIG. 15 is shown illustrating features of the fixation element 570. The fixation element 570 includes one or more appendages 572 or tines. These appendages 572 are generally formed of a biocompatible material. In some embodiments, the appendages sweep backward, away from the distal end 564 of the lead. In some embodiments, the angle 574 between the major axis of the appendages and the major axis of the lead body is less than about ninety degrees. The surface of the appendages can include topographical features configured to modulate the behavior of host cells. For example, the surfaces of the appendages can include any of the various types of topographical features described herein with respect to other embodiments. In some embodiments, the topographical features on the appendages are configured to increase adherence of host cells and thus aid in the anchoring functionality provided by the passive fixation element.

The fixation element illustrated in FIGS. 15-16 is one example of a passive fixation element. However, it will be appreciated that embodiments of the invention can also include leads with other types of passive fixation elements that include surfaces with topographical features, such as passive fixation elements with spiral or curved shapes at the distal part of the lead body. In addition, it will be appreciated that embodiments of the invention can also include leads with active fixation elements that include surfaces with topographical features.

Figure 17:
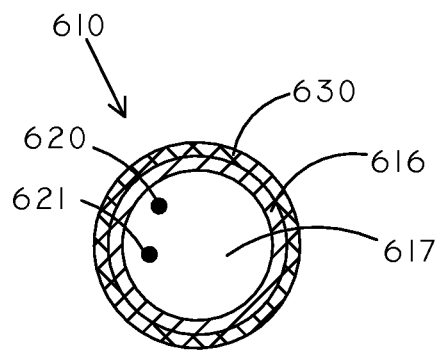
FIG. 17 is a schematic cross-sectional view of a lead in accordance with an embodiment of the invention.

In some embodiments, a cellular modulation segment with topographical surface features can completely surround a lead. Referring now to FIG. 17, a cross-sectional view of a lead 610 is shown in accordance with another embodiment of the invention. The lead 610 includes an outer layer 616 defining a lumen 617. The lead 610 further includes a first electrical conductor 620 and a second electrical conductor 621 disposed within the lumen 617 of the outer layer 616. The lead 610 also includes a cellular modulation segment 630 on the external surface of the outer layer 616. In this embodiment, the cellular modulation segment 630 completely surrounds the outer layer 616.

Figure 18:
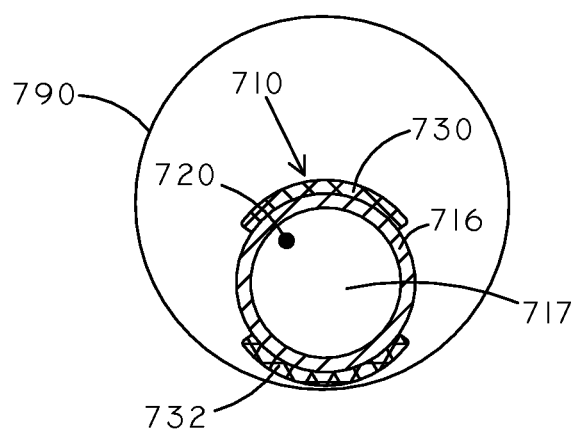
FIG. 18 is a schematic cross-sectional view of a lead in accordance with an embodiment of the invention.

In other embodiments, a cellular modulation segment can be disposed on only certain axial portions of the exterior surface of a lead. In addition, multiple distinct cellular modulation segments can be disposed in different positions axially around the lead. Referring now to FIG. 18, a cross-sectional view of a lead 710 is shown in accordance with another embodiment of the invention. The lead 710 includes an outer layer 716 defining a lumen 717. The lead 710 further includes a first electrical conductor 720 disposed within the lumen 717 of the outer layer 716.

The lead 710 includes a first cellular modulation segment 730 on the external surface of the outer layer 716. The lead 710 includes a second cellular modulation segment 732 on the external surface of the outer layer 716. This arrangement of cellular modulation segments can allow for additional configurations of cell behavior modulation. By way of example, in a circumstance where one side of a lead 710 is to be disposed against a vascular wall 790, it may be desirable to boost adherence of cells lining the vascular wall 790 to the lead 710, while simultaneously preventing them from fully enveloping the lead 710. In such a circumstance, the second cellular modulation segment 732, the one facing the vascular wall 790, can include topological surface features configured to enhance cellular adherence while the first cellular modulation segment 730, the one away from the vascular wall 790, can include topological surface features configured to prevent cell migration and/or reduce cell adherence. In this manner, the lead can be secured in place with a desired amount of strength but not become so embedded in tissue as to make an explant procedure unduly difficult, should it become necessary.

It will be appreciated that leads as described herein can be disposed in various places within the body, both intravascularly and extravascularly. In some embodiments, the lead can be configured to pass into the heart, typically through the superior vena cava, and then into the right atrium and/or the right ventricle. In some embodiments, the lead can be configured to pass into the coronary venous system where the left side of the heart, such as the left ventricle, is within sufficient proximity that electrical stimulation pulses can capture the left ventricle.

Figure 19:
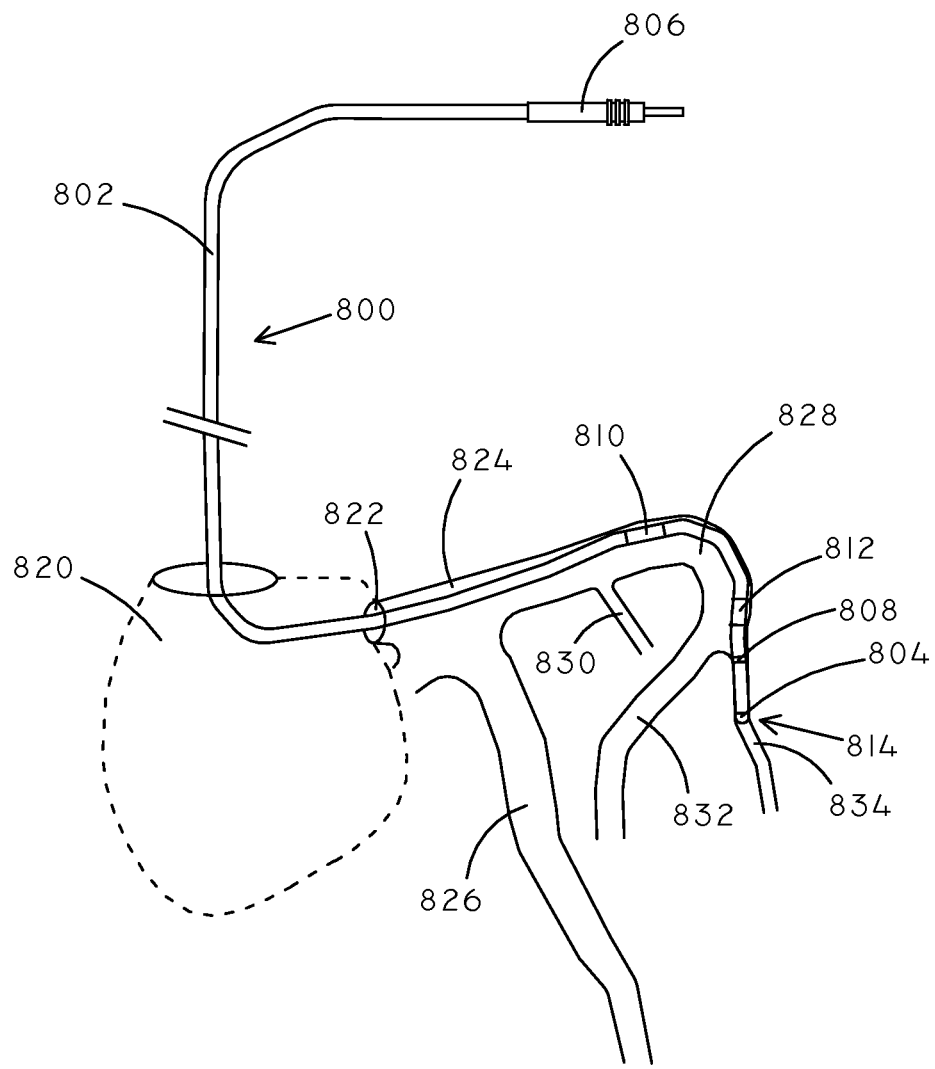
FIG. 19 is a schematic view of a lead in accordance with an embodiment of the invention disposed within the coronary venous system.

Referring now to FIG. 19, a schematic view is shown of a lead 800 disposed within the coronary venous system. The lead includes a lead body 802 and a terminal pin 806. The lead 800 also includes a first electrode 804 and a second electrode 808. The lead 800 passes into the heart through the superior vena cava and into the right atrium 820. The lead then passes through the coronary sinus ostium 822 and into the coronary sinus itself 824. Tributaries of the coronary sinus include the middle cardiac vein 826, the great cardiac vein 828, the posterior vein of the left ventricle 830, the lateral vein of the left ventricle 834, and the anterior interventricular vein 832, amongst others. In this embodiment, the lead passes through the great cardiac vein 828 and into the lateral vein of the left ventricle 834. However, it will be appreciated that the lead can actually be disposed in many specific areas of the coronary venous system, depending of the preferences of the clinician, the specific anatomy of the patient, and various other factors.

In the embodiment shown in FIG. 19, it will be appreciated that the lead includes a first cellular modulation segment 810 and a second cellular modulation segment 812 that are both disposed within the coronary venous system when the lead is properly positioned. Specifically, in an embodiment, one or both of the first and second cellular modulation segments are disposed within about 7 to 10 centimeters of the distal end 814 of the lead. In some embodiments, a cellular modulation segment configured to aid in anchoring the lead in place is disposed within about 4 centimeters of the distal end of the lead.

Figure 20:
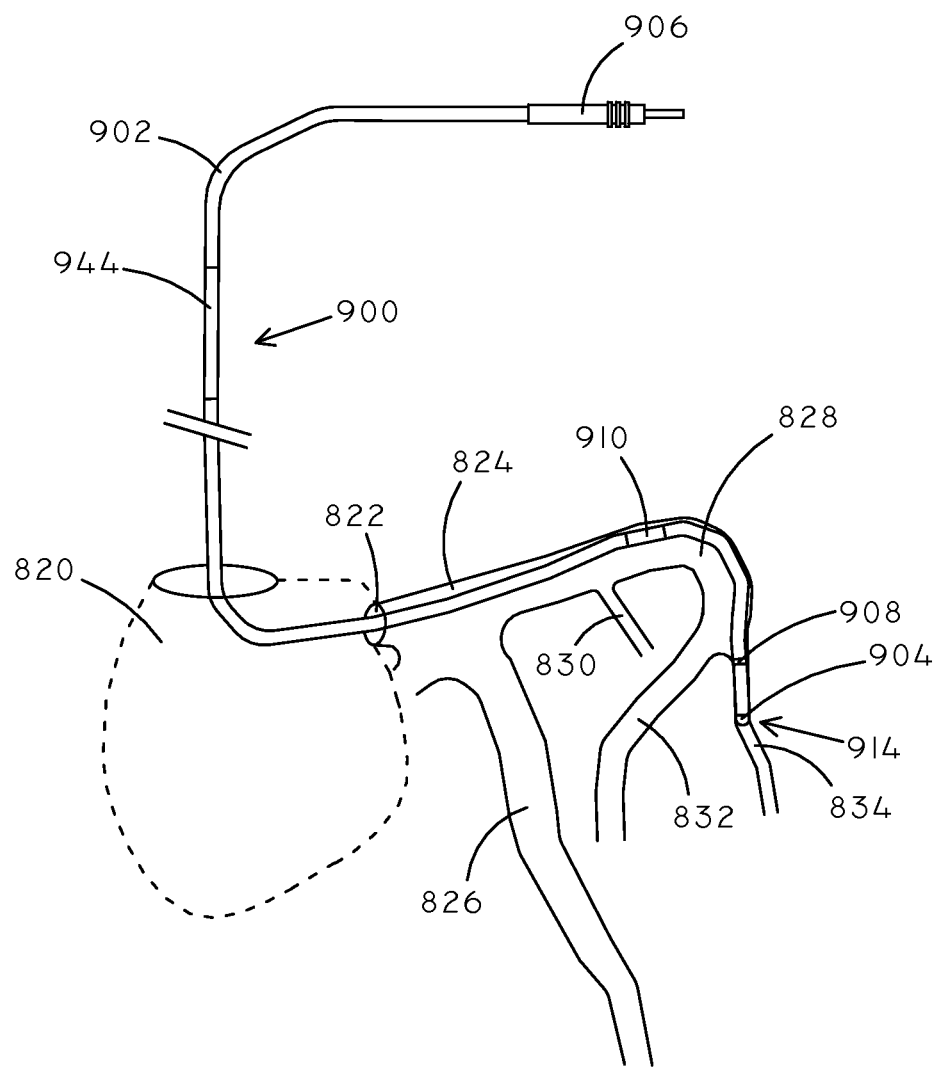
FIG. 20 is a schematic view of a lead in accordance with another embodiment of the invention disposed within the coronary venous system.

As described above, some embodiments of leads included herein can include multiple cellular modulation segments that are configured differently to produce different effects on host cell behavior. Referring now to FIG. 20, a schematic view is shown of a lead disposed within the coronary venous system in accordance with another embodiment of the invention. The lead 900 includes a lead body 902 and a terminal pin 906. The lead 900 also includes a first electrode 904 and a second electrode 908, both disposed near the distal end 914 of the lead body 902. The lead passes into the heart through the superior vena cava and into the right atrium 820. The lead then passes through the coronary sinus ostium 822 and then into the coronary sinus 824. In this embodiment, the lead passes through the great cardiac vein 828 and into the lateral vein of the left ventricle 834. The portion of the lead 900 designed to be disposed within the coronary venous system can be referred to as the distal segment of the lead 900, while the remainder of the lead 900 can be referred to as the transmission segment.

The lead 900 of FIG. 20 includes a first cellular modulation segment 910 that is positioned such that it is disposed within the coronary venous system when the lead is properly positioned. Specifically, the first cellular modulation segment is disposed on the distal segment of the lead 900. In this embodiment, the first cellular modulation segment 910 includes features configured to increase adherence of cells, in order to anchor the electrodes of the lead 900 in place. The lead 900 of FIG. 20 also includes a second cellular modulation segment 944 that is positioned such that it is on an area of the lead 900 that is not within the coronary venous system, such as in the vasculature between the subclavian vein and the superior vena cava. Specifically, the second cellular modulation segment 944 is disposed on the transmission segment of the lead 900. In this position, because of the flexible nature of leads in general, adherence of cells would not be beneficial because they would not serve to keep the electrodes positioned as desired within the coronary venous system. As such, adherence of cells in this position on the lead would generally be undesirable because it would serve to increase the amount of force required to remove the lead during an explant procedure. Therefore, in this embodiment, the second cellular modulation segment 944 includes features configured to prevent or reduce the adherence of cells, in order to prevent attachment of this segment of the lead to the vasculature in which it is disposed.

Figure 21:
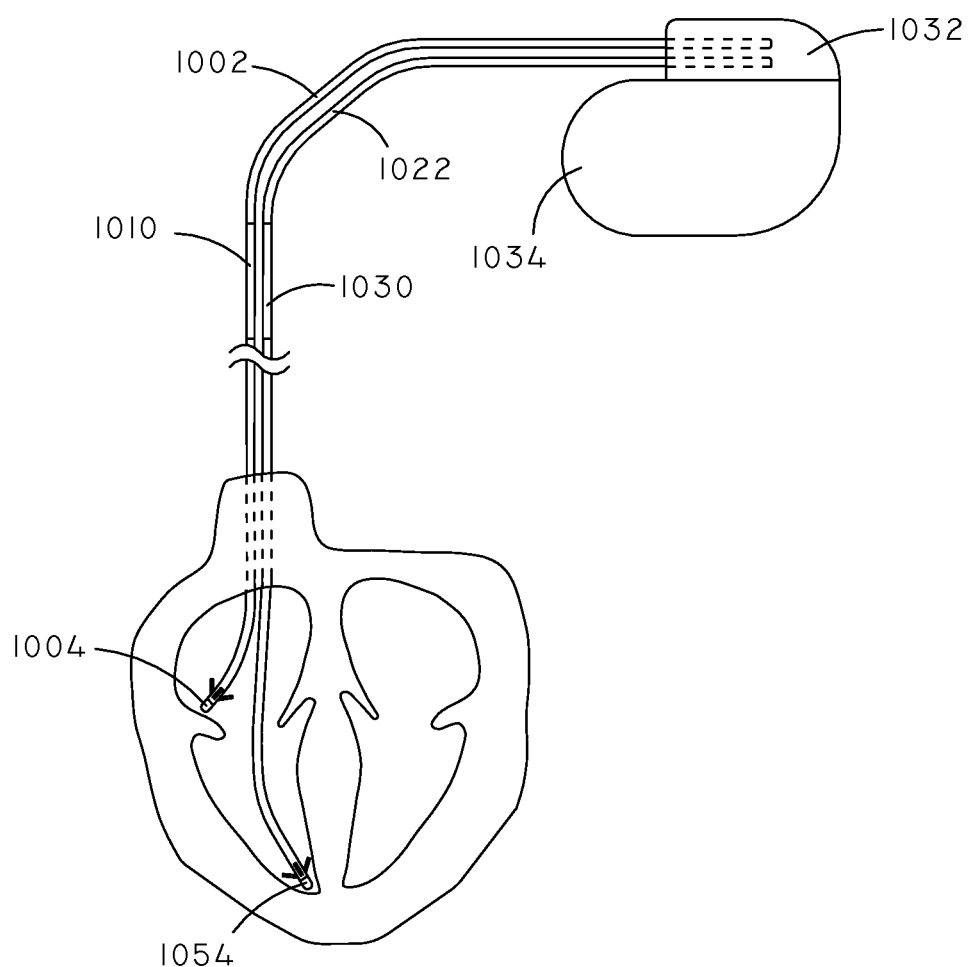
FIG. 21 is a schematic view of an implantable medical system in accordance with an embodiment of the invention.

Embodiments of the invention can include electrical stimulation systems that include one or more cellular modulation segments. Exemplary electrical stimulation systems can specifically include CRM devices, such as pacemakers, implantable cardioverter defibrillators (ICDs), cardiac resynchronization therapy (CRT) devices, and the like. Exemplary electrical stimulation systems can also include neural stimulation devices. Referring now to FIG. 21, an electrical stimulation system with cellular modulation segments is shown in accordance with an embodiment of the invention. The electrical stimulation system includes a pulse generator 1034 and a header 1032 coupled to the pulse generator 1034. The header 1032 is, in turn, coupled to a first lead 1002 and a second lead 1022. The first lead 1002 is in electrical communication with a first electrode 1004. The second lead 1022 is in electrical communication with a second electrode 1054. A first cellular modulation segment 1010 is disposed on the first lead 1002. A second cellular modulation segment 1030 is disposed on the second lead 1022.

Figure 22:
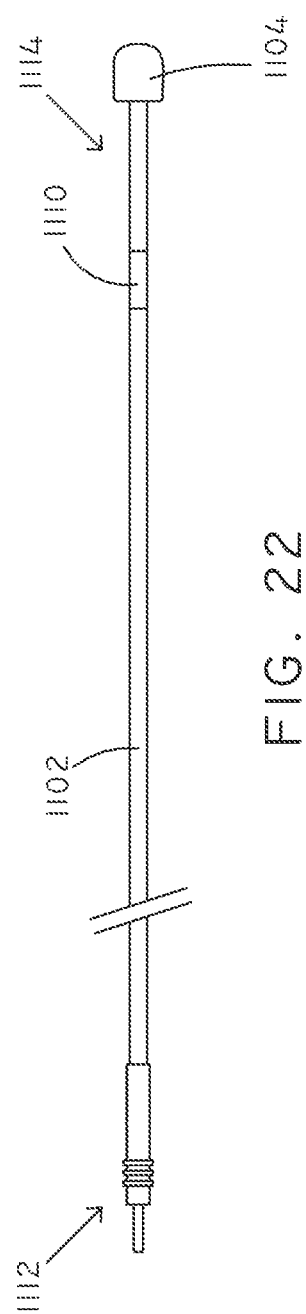
FIG. 22 is a schematic view of a sensor lead in accordance with an embodiment of the invention.

In some embodiments, leads as described herein can be electrical stimulation leads (or catheters). In other embodiments, leads can include sensor leads. A sensor lead is a lead used to couple an implantable medical device with an implantable sensor. Referring now to FIG. 22, an embodiment of a sensor lead is shown in accordance with an embodiment of the invention. The lead includes a lead body 1102 with a proximal end 1112 and a distal end 1114. A conductor, such as an electrical conductor or an optical conductor, can be disposed within the lead body. In this embodiment, the lead is configured to be coupled to an implantable sensor 1104. The implantable sensor 1104 can include various types of sensors such as pressure sensors, accelerometers, chemical sensors, and the like. The lead can include a cellular modulation segment 1110. The cellular modulation segment 1110 can include topographical surface features configured to modify the behavior of host cells.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. An implantable lead comprising:
a lead body having a proximal end and a distal end, the lead body comprising an outer layer defining a lumen, the lead body further comprising a first electrical conductor disposed within the lumen of the outer layer, the lead body having a lengthwise axis extending between the proximal end and the distal end;
a first electrode coupled to the lead body, the first electrode in electrical communication with the first electrical conductor;
a first cellular modulation segment on the external surface of the lead body configured to increase cellular adhesion, the first cellular modulation segment comprising topographic surface features configured to modulate cellular responses, the topographic surface features comprising a plurality of ridges with a pitch between about 20 nm and about 2000 nm, wherein the ridges are oriented perpendicular to the lengthwise axis of the lead body, the first cellular modulation segment disposed within 10 centimeters of the distal end of the lead body; and
a second cellular modulation segment on the external surface of the lead body configured to reduce cellular adhesion, the second cellular modulation segment comprising topographic surface features to modulate cellular responses, the topographic surface features comprising a plurality of ridges oriented perpendicular to the lengthwise axis of the lead body, the second cellular modulation segment disposed on a different portion of the lead body than the first cellular modulation segment.

2. The implantable lead of claim 1, wherein the plurality of ridges are evenly spaced.

3. The implantable lead of claim 1, the plurality of ridges comprising a polygonal shape in cross-section.

4. The implantable lead of claim 1, the plurality of ridges comprising a saw tooth shape in cross-section.

5. The implantable lead of claim 1, the outer layer comprising a material selected from the group consisting of silicone and polyurethane.

6. The implantable lead of claim 1, the cellular modulation segment integral with the outer layer.

7. The implantable lead of claim 1, the cellular modulation segment coupled to the external surface of the outer layer.

8. The implantable lead of claim 7, the cellular modulation segment comprising a metal foil.

9. The implantable lead of claim 1, the cellular modulation segment disposed on the first electrode.

10. The implantable lead of claim 1, wherein the pitch of the ridges is about 250 nm or less.

11. An implantable lead comprising:
a lead body having a proximal end and a distal end, the lead body comprising a transmission segment and a separate distal segment, the lead body comprising an outer layer defining a lumen, the lead body further comprising a first electrical conductor disposed within the lumen of the outer layer;
a first electrode coupled to the lead body, the first electrode in electrical communication with the first electrical conductor;

a first cellular modulation segment disposed in the distal segment on the external surface of the lead body configured to increase cellular adhesion, the first cellular modulation segment comprising topographic surface features comprising a plurality of ridges, a second cellular modulation segment disposed in the transmission segment on the external surface of the lead body configured to decrease cellular adhesion, the second first cellular modulation segment comprising topographic surface features comprising a plurality of ridges with a pitch between about 20 nm and about 2000 nm, wherein the topographic surface features of the second cellular modulation segment are different than the topographic surface features of the first cellular modulation segment.

\* \* \* \* \*